(12) United States Patent
Kawano et al.

(10) Patent No.: US 8,454,495 B2
(45) Date of Patent: Jun. 4, 2013

(54) CAPSULE MEDICAL APPARATUS

(75) Inventors: Hironao Kawano, Hachioji (JP);
Hironobu Takizawa, Hachioji (JP);
Akio Uchiyama, Yokohama (JP);
Hidetake Segawa, Hachioji (JP);
Manabu Fujita, Hino (JP); Akira Kikuchi, Yokohama (JP); Takeshi Yokoi, Hino (JP)

(73) Assignee: Olympus Corporation, Tokyo (JP)

( * ) Notice: Subject to any disclaimer, the term of this patent is extended or adjusted under 35 U.S.C. 154(b) by 2601 days.

(21) Appl. No.: 11/201,829

(22) Filed: Aug. 11, 2005

(65) Prior Publication Data

US 2005/0272973 A1 Dec. 8, 2005

Related U.S. Application Data

(63) Continuation of application No. PCT/JP2004/002189, filed on Feb. 25, 2004.

(30) Foreign Application Priority Data

Feb. 25, 2003 (JP) ................................. 2003-047755

(51) Int. Cl.
*A61B 1/00* (2006.01)
*A61B 1/04* (2006.01)
*A61B 1/06* (2006.01)

(52) U.S. Cl.
USPC ............................. 600/118; 600/103; 600/160

(58) Field of Classification Search
USPC .......................... 600/101, 109, 117, 118, 160
See application file for complete search history.

(56) References Cited

U.S. PATENT DOCUMENTS

| 6,764,440 | B2 * | 7/2004 | Iddan et al. | 600/109 |
| 2001/0051766 | A1 * | 12/2001 | Gazdzinski | 600/309 |
| 2002/0032366 | A1 * | 3/2002 | Iddan et al. | 600/117 |
| 2002/0177782 | A1 | 11/2002 | Penner | |
| 2003/0020810 | A1 * | 1/2003 | Takizawa et al. | 348/68 |

FOREIGN PATENT DOCUMENTS

| EP | 1 277 493 A2 | 1/2003 |
| JP | 2-224650 | 9/1990 |
| JP | 2849131 | 11/1998 |
| JP | 2003-038424 | 2/2003 |
| WO | WO 95/29735 | 11/1995 |
| WO | WO 01/35814 A1 | 5/2001 |
| WO | WO 01/65995 A2 | 9/2001 |
| WO | WO 03/009739 A2 | 2/2003 |

\* cited by examiner

*Primary Examiner* — Philip R Smith
(74) *Attorney, Agent, or Firm* — Scully, Scott, Murphy & Presser, P.C.

(57) ABSTRACT

A capsule medical apparatus includes a capsule exterior member and a sensor that can detect the change of an atmospheric physical quantity caused outside the exterior member in the non-contact state, and performs, based on the temporary change in atmospheric physical quantity detected by the sensor, at least one of first control for switching operation from the ON-state of energy supply to the electric circuit from the battery to the OFF-state of the energy supply and of second control for switching operation from the OFF-state of the power supply to the ON-state of the power supply, and holds the state of energy supply switched by the control until another change of atmospheric physical quantity is detected.

9 Claims, 15 Drawing Sheets

CAPSULE MEDICAL APPARATUS

CROSS REFERENCE TO RELATED APPLICATION

This application is a continuation application of PCT/JP2004/002189 filed on Feb. 25, 2004 and claims the benefit of Japanese Application No. 2003-047755 filed in Japan on Feb. 25, 2003, the entire contents of each of which are incorporated herein by their reference.

BACKGROUND OF THE INVENTION

1. Field of the Invention

The present invention relates to a capsule medical apparatus with a capsule shape, for examining the inside of the living body.

2. Description of the Related Art

PCT WO 01-35814A1 Publication discloses an example of collecting images, as one example of capsule medical apparatuses with a capsule shape for easy swallowing by a patient, for examining the inside of the living body.

In the example (first example), a capsule main body for collecting the images are covered with a package before use. A magnet is set to the package side. In the use for image collection, the capsule main body is pulled out from the package and is separated from the package, thereby setting a switch circuit from OFF to the ON with magnetic force of magnet.

Further, Japanese Patent Publication (Patent No. 2849131) discloses an example of ultrasonic diagnosis, as another example of the capsule medical apparatuses.

In the example (second example), an external trigger signal or the like is received to turn on/off the power of the capsule main body.

SUMMARY OF THE INVENTION

According to the present invention, a capsule medical apparatus includes a capsule exterior member and a sensor that can detect the change of an atmospheric physical quantity caused outside the exterior member in the non-contact state, and performs, based on the temporary change in atmospheric physical quantity detected by the sensor, at least one of first control for switching operation from the ON-state of energy supply to the electric circuit from the battery to the OFF-state of the energy supply and of second control for switching operation from the OFF-state of the energy supply to the ON-state of the energy supply, and holds the state of energy supply switched by the first control or second control.

DESCRIPTION OF THE PREFERRED EMBODIMENTS

Hereinbelow, embodiments of the present invention will be described with reference to the drawings.

(First Embodiment)

Figure 1:
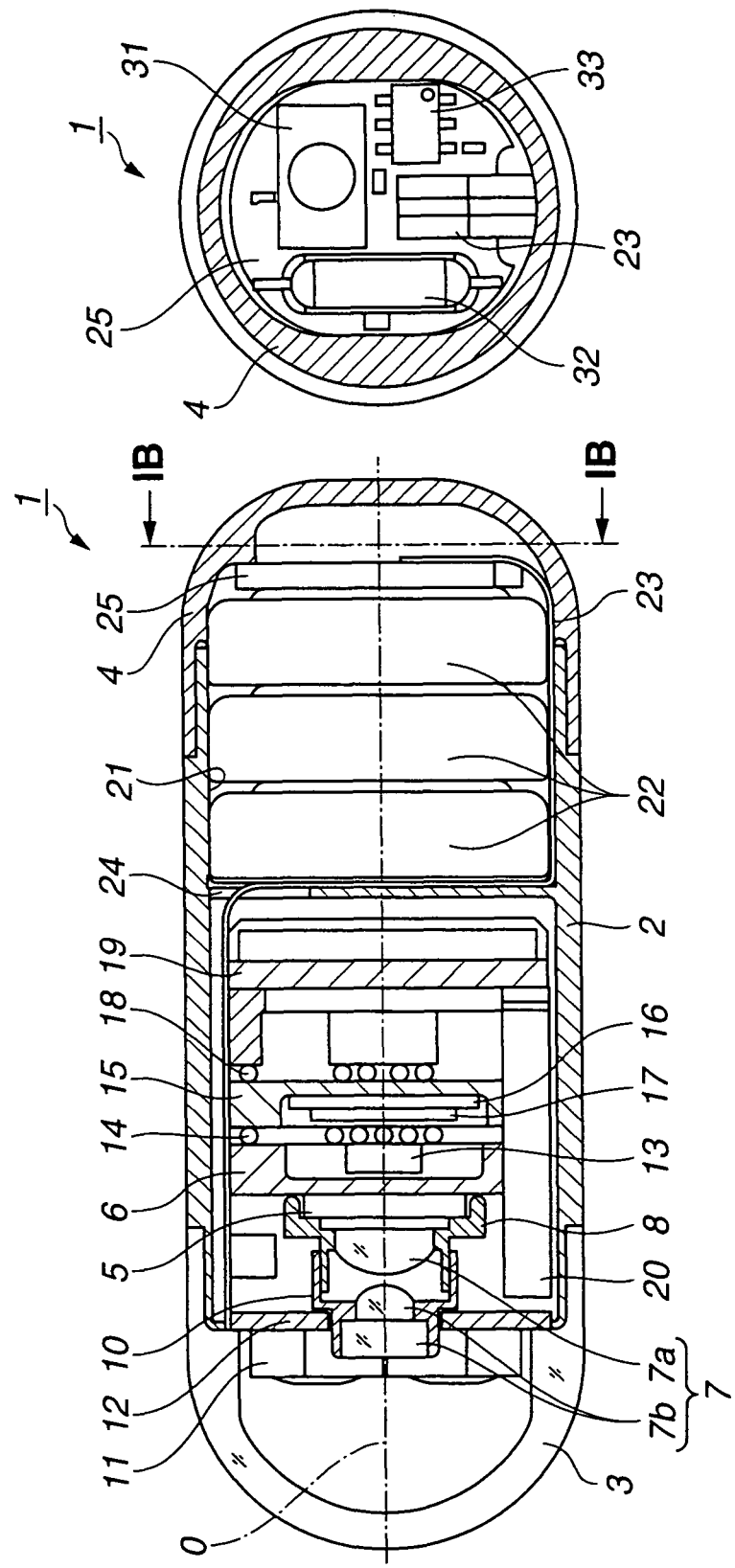
FIG. 1A is a longitudinal cross-sectional view showing the internal structure of a capsule medical apparatus according to a first embodiment of the present invention.
FIG. 1B is a cross-sectional view showing the structure of a switch substrate in the capsule medical apparatus according to a first embodiment of the present invention.
Figure 2:
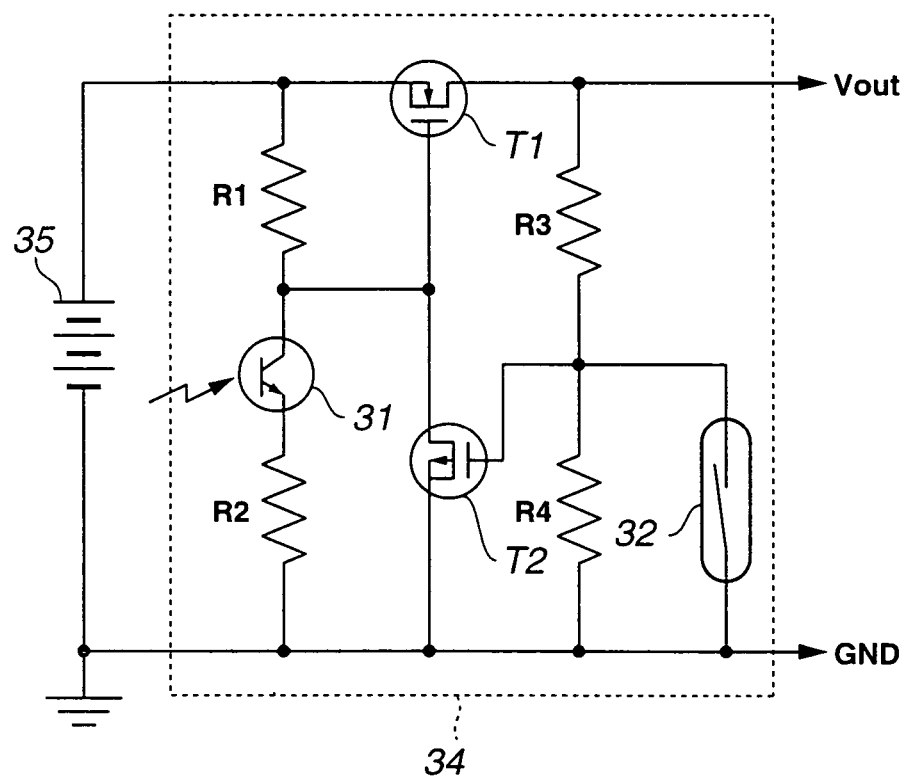
FIG. 2 is a circuit diagram showing the structure of a switch circuit in the capsule medical apparatus according to the first embodiment.
Figure 3:
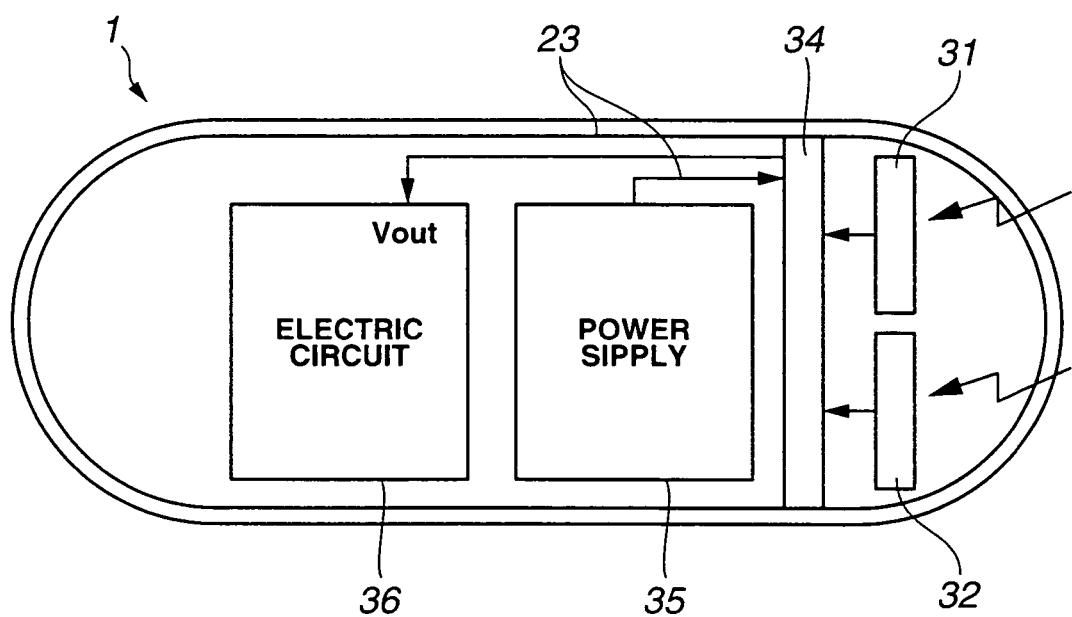
FIG. 3 is a diagram showing the schematic structure for explaining the operation of the capsule medical apparatus according to the first embodiment.

FIGS. 1A to 3 relate to the first embodiment. FIGS. 1A and 1B show the internal structure of a capsule medical apparatus according to the first embodiment, FIG. 1A shows a longitudinal cross-sectional view, FIG. 1B shows the structure of a switch substrate using an IB-IB cross-section in FIG. 1A, FIG. 2 shows the circuit structure of a switch circuit, and FIG. 3 shows the schematic structure for explaining the operation of the capsule medical apparatus.

Referring to FIG. 1A, a capsule medical apparatus 1 according to the first embodiment of the present invention forms a capsule container sealed with the watertight structure by covering the front end of a cylindrical capsule main body (hereinafter, abbreviated to a min body) 2 with a transparent and semi-spherical distal-end cover 3 and by covering the rear end of the main body 2 with a circular rear cover 4. Further, the capsule medical apparatus 1 comprises image pickup means, as will be described later.

In the capsule container, a CMOS sensor 5, serving as image pickup means, is mounted on a sensor substrate 6 to form a CMOS module in the center thereof, facing the distal-end cover 3.

A fixing frame 8 having a fixing side lens 7a of an objective lens system 7, (serving as a lens closest to the CMOS sensor 5), is fixed to an image area (image pickup area) in front of the CMOS sensor 5. A movable frame 10 having a movable side lens 7b of the objective lens system 7 is fit into a cylindrical portion of the fixing frame 8, with the focusing operation being adjusted.

Thus, the objective lens system 7 forms an image of a subject, such as a luminal portion in the body cavity, in an image area of the CMOS sensor 5, in the focusing state.

An LED substrate 12 having a white LED 11, serving as illuminating means, is fit and fixed to a hole portion arranged in the center of a cylindrical portion of the movable frame 10. The image pickup range of the objective lens system 7 is illuminated substantially uniformly by the white LEDs 11 arranged at four portions around the objective lens system 7.

A caved portion is formed on the rear surface of the sensor substrate 6, and an electrical part, such as an IC chip 13, is flip-mounted. On the rear surface of the sensor substrate 6, an image pickup processing and control substrate 15 is connected via a connecting member containing a soldering ball 14, and the image pickup processing and control substrate 15 performs the signal processing and control operation of an output signal picked-up by the CMOS sensor 5.

The image pickup processing and control substrate 15 has a caved portion in front thereof, and a first bear-chip 16, serving as an electronic part, e.g., an IC chip, is flip-mounted to the caved portion. Further, a second bear-chip 17 having an IC chip with a different function, is mounted, by wire bonding, to the top of the bear chip 16.

The back side of the image pickup processing and control substrate 15 is connected to a communication substrate (wireless substrate) 19 via a connecting member having a soldering ball 18. Electronic parts are mounted on both sides of the communication substrate 19, thereby forming communication modules based on Blue-tooth (TM) system wireless manner.

As mentioned above, the main body 2 comprises, in the axial direction thereof, the sensor substrate 6, the image pickup processing and control substrate 15, and the communication substrate 19. In this case, the sensor substrate 6 is electrically connected to the image pickup processing and control substrate 15 by the soldering ball 14 at the interval of the soldering ball 14 (that is, the interval within that of the soldering ball 14). The image pickup processing and control substrate 15 is connected to the communication substrate 19 by the soldering ball 18 at the interval of the soldering ball 18.

As mentioned above, the substrates with different functions are connected with small intervals and high density, and an electronic-circuit block is structured with functions of illumination, image pickup operation, and external transfer of the picked-up image signal. Thus, since the length of the capsule medical apparatus 1 in the axial direction is short, the capsule medical apparatus 1 easily-swallowed by a patient is realized.

Sides on the bottom side of the LED substrate 12, the sensor substrate 6, and the image pickup processing and control substrate 15 are partly notched, and an antenna 20 connected to the communication substrate 19 is arranged along the notched portion. In this case, the antenna 20 is arranged in parallel with an optical axis O of the objective lens system 7.

Then, an image signal that is photoelectrically converted by the CMOS sensor 5 is transmitted to an external extracorporeal device 52 (refer to FIG. 11) via the communication substrate 19, and the period for illumination or image pickup operation is changed in response to an instruction signal from the extracorporeal device 52.

On the back of the communication substrate 19, the main body 2 and the rear cover 4 form a battery accommodating unit 21. Three batteries 22 are accommodated in the battery accommodating unit 21.

Along the inside of the main body 2 on the opposite of the antenna 20, a flexible substrate 23, serving as a flexible substrate, with the flexibility is arranged, the distal end of the flexible substrate 23 is connected to the LED substrate 12 and is bent, at an angle of 90° by an opening 24 arranged to the back side of the communication substrate 19. The bent portion is inserted in the battery accommodating unit 21, and comes into contact with the positive portion of the battery 22 in the halfway (a conductive pattern is exposed at the contact portion to the positive of the battery 22).

Therefore, the flexible substrate 23 has a bending manner, in advance, so that the back portion (rear end of the communication module) is bent. Thus, the assembling operation of the flexible substrate 23 is easy.

Further, the flexible substrate 23 is bent as mentioned above, and is conductive to the positive of the battery 22 in the halfway. The flexible substrate 23 is bent at an angle of 90° along the side of the battery accommodating unit 21 on the antenna 20 side, thereby being extended to the rear side.

The rear end is connected to a switch substrate 25 arranged between the negative of the battery 22 and the inside of the caved portion of the rear cover 4.

The sides on the bottom of the LED substrate 12 and the sensor substrate 6 are partly notched. Along the notched portion, the antenna 20 connected to the communication substrate 19 is arranged. In this case, the antenna 20 is arranged in parallel with the optical axis O of the objective lens system 7.

On the switch substrate 25, referring to FIG. 1B, an end of the pattern of the end of the flexible substrate 23 is soldered to the center of the switch substrate 25 on one side of the switch substrate 25, specifically, on the part mounting surface, serving as the rear cover 4 side. On the top thereof, an optical sensor 31 is mounted. On the left, a magnetic sensor (specifically, reed switch) 32 is mounted. On the right, an IC chip 33 is mounted. In addition, a chip resistor is mounted.

The parts mounted on the switch substrate 25 and the circuit pattern form a switch circuit 34 as shown in FIG. 2. Referring to FIG. 2, the switch circuit 34 controls the ON/OFF operation of the power supply from a power supply 35 (having three batteries 22) to the communication substrate 19 (via the pattern of the flexible substrate 23) and of the power supply to a power end (Vout) of an electric circuit 36 (refer to FIG. 3) functioning by the power supply from the battery 22, in accordance with the change in atmospheric physical quantity to the sensors 31 and 32.

The switch circuit 34 shown in FIG. 2 is a circuit basically having a function for supplying the power from the power supply 35 to the electric circuit 36 by the light input to the optical sensor (specifically, photo transistor) 31, serving as a first sensor, that is, a switch function for switching the power switch from the OFF-operation to the ON-operation, and a switch function for switching the power switch from the ON-operation to the OFF-operation by applying magnetic force to the magnetic sensor 32, serving as a second sensor.

FIG. 3 simply shows the function of the switch circuit 34 in the capsule medical apparatus 1 shown in FIG. 1. The switch circuit 34 is set to the state for supplying the power by the switch circuit 34 electrically arranged between the power supply 35 and the electric circuit 36 based on the detecting output by the light input to the photo transistor 31. Then, the switch circuit 34 stops the power supply based on the detecting output by applying magnetic force to the magnetic sensor 34.

According to the first embodiment, the light input (light irradiation) to the photo transistor 31 and the magnetic application to the magnetic sensor 32 are performed by temporary non-contact operation, thereby switching the switch circuit 34 to the ON-operation from the OFF-operation and to the OFF-operation from the ON-operation.

Specifically, referring to FIG. 2, in the switch circuit 34, the positive of the power supply 35 is connected to a power terminal Vout, serving as an output terminal of the switch circuit 34, via a source and a drain of a P-channel MOS transistor T1, and is connected to the ground (GND) via a serial circuit of a resistor R1, a collector and an emitter of the photo transistor 31, and a resistor R2. The negative of the power supply 35 is connected to the GND.

A connecting point between the resistor R1 and the collector of the photo transistor 31 is connected to a gate of the transistor T1. The gate is connected to a drain of an N-channel MOS transistor T2, and a source is connected to the GND.

The power terminal Vout is connected to the GND via a serial circuit of resistors R3 and R4. Connecting points of the resistors R3 and R4 are connected to a gate of the transistor T2, and are connected to the GND via a reed switch 32.

When the light is not incident on the photo transistor 31, in the switch circuit 34, it is non-conductive, that is, OFF between the collector and the emitter of the photo transistor 31. The collector becomes the H level. Thus, the transistor T1 whose gate is connected to the collector is non-conductive (OFF), thereby keeping the state for preventing the power supply from the power supply 35 to the power terminal Vout, that is, OFF-state of the power switch.

When the light is incident on the photo transistor 31, the collector of the photo transistor 31 is set to the L level from the H level. The potential of the gate of the transistor T1 is changed to the L level from the H level, thereby making the transistor T1 conductive (ON). The on-operation of the transistor T1 sets the potential divided by the resistors R3 and R4 (for the ON/OFF operation of the transistor T2) from the L level to the H level. Then, the transistor T2 is switched on, thereby reducing the potential of the gate of the transistor T1 and the transistor T1 keeps the ON-state. After that, the transistor T1 keeps the ON-state without the incident light, and power from the power supply 35 is supplied to the power terminal Vout. That is, the power switch keeps the ON-state.

Meanwhile, in the ON-state of the power switch, the magnetic force is applied to a reed switch 32 from magnet, thereby operating the reed switch 32 by the magnetic force. A switch contact of the reed switch 32 is switched-on from the OFF-state. The ON-state of the switch contact enables a gate of the transistor T2 to be at the L level from the H level. The transistor T2 changes from the ON-state to the OFF-state.

Then, the gate of the transistor T1 is set to the H level from the L level, thereby setting the transistor T1 to the OFF-operation. The off-operation of the transistor T1 enables the power terminal Vout to be at the L level. Then, the transistor T2 keeps the OFF-state, irrespective of the ON/OFF-operation of the switch contact of the reed switch 32, and the transistor T1 keeps the OFF-state.

According to the first embodiment, the light is temporarily inputted to the optical sensor 31 in the non-contact state, thereby setting the switch circuit 34 to the ON-state from the OFF-state. After setting to the ON-state, the light is not continuously inputted. Therefore, the user's convenience is improved. The switch circuit 34 is set to the OFF-state from the ON-state by temporarily applying the magnetic force to the reed switch 32. Therefore, the user's convenience is improved.

Further, it is possible to certainly prevent the erroneous operation of the ON-operation and the OFF-operation because of using the sensor for detecting the atmospheric physical quantity varied depending on the on-operation and the OFF-operation.

Referring to FIG. 2, the optical sensor 31 is used as a sensor for ON-operation and the magnetic sensor 32 is used as a sensor for OFF-operation. Further, a magnetic sensor similar to the magnetic sensor 32 is used for replacement at the optical sensor 31, thereby forming a sensor for ON-operation.

An optical sensor similar to the optical sensor 31 is used for replacement at the magnetic sensor 32, as a sensor for OFF-operation. That is, two sensors with the same types perform the operation from the OFF-operation to the ON-operation, and from the ON-operation to the OFF-operation.

(Second Embodiment)

Figure 4:
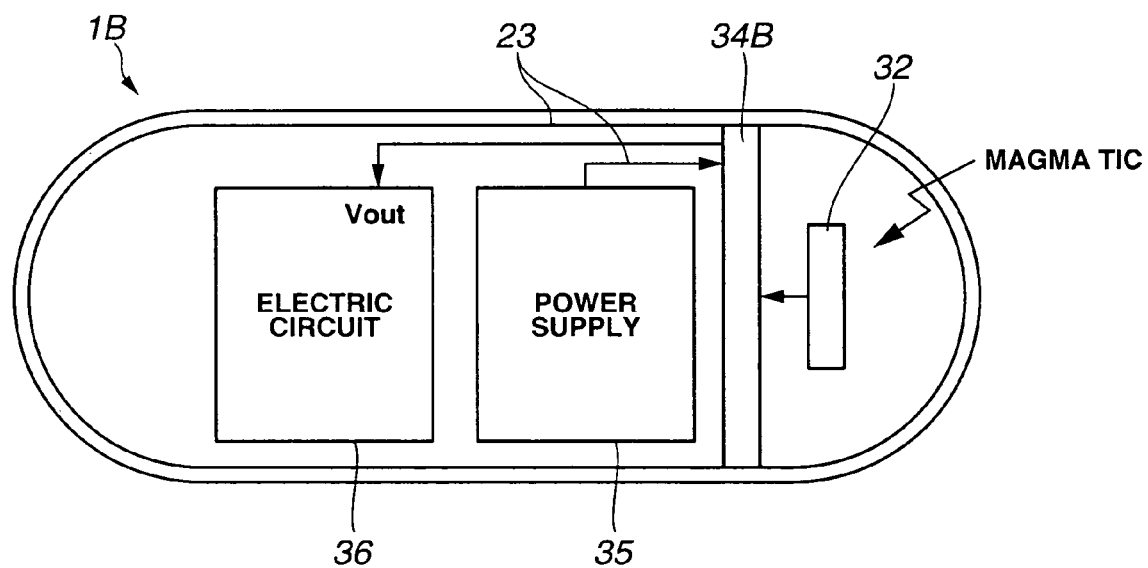
FIG. 4 is a diagram showing the schematic structure of a capsule medical apparatus according to a second embodiment of the present invention.
Figure 5:
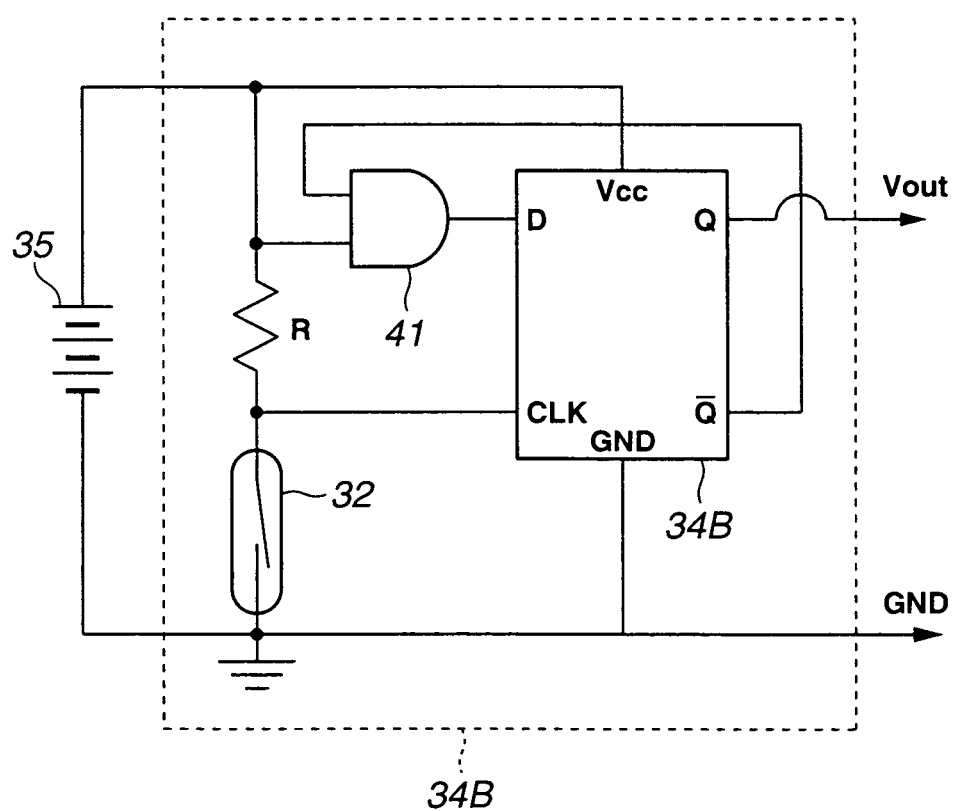
FIG. 5 is a circuit diagram showing the structure of a switch circuit in the capsule medical apparatus according to the second embodiment.

Next, a description is given of the second embodiment of the present invention with reference to FIGS. 4 and 5. FIG. 4 shows the schematic structure of a capsule medical apparatus 1B according to the second embodiment of the present invention. A switch circuit 34B in the capsule medical apparatus 1B has only one sensor, such as only the reed switch 32.

FIG. 5 shows the specific circuit structure of the switch circuit 34B according to the second embodiment. Referring to FIG. 5, the positive of the power supply 35 is connected to one input terminal of an AND gate 41 forming the switch circuit 34B, and is further connected to a power terminal Vcc of a D-type flip-flop 42. Furthermore, the positive of the power supply 35 is connected to a resistor R and the GND via the reed switch 32 serially connected to the resistor R.

A connecting point between the resistor R and the reed switch 32 is connected to a clock input terminal CLK of the flip-flop 42, and an inverting output terminal of the flip-flop 42 is connected to another input terminal of the AND gate 41. An output of the AND gate 41 is applied to a data input terminal D of the flip-flop 42. An output terminal Q is connected to an output terminal of the switch circuit 34B, that is, the power terminal Vout. A GND terminal of the flip-flop 42 is connected to the negative of the power supply 35, and the negative is connected to the GND of an electric circuit.

With the above-mentioned structure according to the second embodiment, the magnetic force is temporarily applied to the reed switch 32, thereby setting the ON-state for supplying the power from the power terminal Vout or setting the OFF-state from the ON-state.

For example, referring to FIG. 5, first the reed switch 32 is in the off-state and the output terminal Q is at the L level. Then, a voltage at the H level is applied to the data input terminal D.

The magnetic force is temporarily applied to the reed switch 32 with the magnet or the like. When the magnet is kept away from the reed switch 32, the reed switch 32 is switched to the OFF-state from the ON-state. Then, a signal applied to the clock input terminal CLK of the flip-flop 42 changes from the L level to the H level with the rising edge. Then, data at the H level at the data input terminal D is outputted from the output terminal Q. In this state, a voltage at the L level is applied to the data input terminal D.

That is, the magnetic force is temporarily applied to the reed switch 32, thereby continuously setting the switch circuit 34B to the ON-state from the OFF-state.

Further, the magnetic force is temporarily applied to the reed switch 32 in this state. When the magnet is kept away from the reed switch 32, the reed switch 32 is switched to the OFF-state from the ON-state. Then, a signal applied to the clock input terminal CLK changes from the L level to the H level with the rising edge. Then, data at the L level at the data input terminal D is outputted from the output terminal Q. In this state, a voltage at the H level is applied to the data input terminal D.

That is, the magnetic force is temporarily applied to the reed switch 32, thereby continuously setting the switch circuit 34B to the OFF-state from the ON-state.

According to the second embodiment, the reed switch 32 can be set from the OFF-operation to the ON-operation and from the ON-operation to the OFF-operation by temporarily input (applying) the atmospheric physical quantity by using one sensor with the simple structure, thereby reducing costs. Incidentally, the optical sensor may be used, in place of the reed switch 32.

(Third Embodiment)

Next, a description is given of the third embodiment of the present invention.

The structure according to third embodiment is obtained by modifying the first embodiment.

Figure 6:
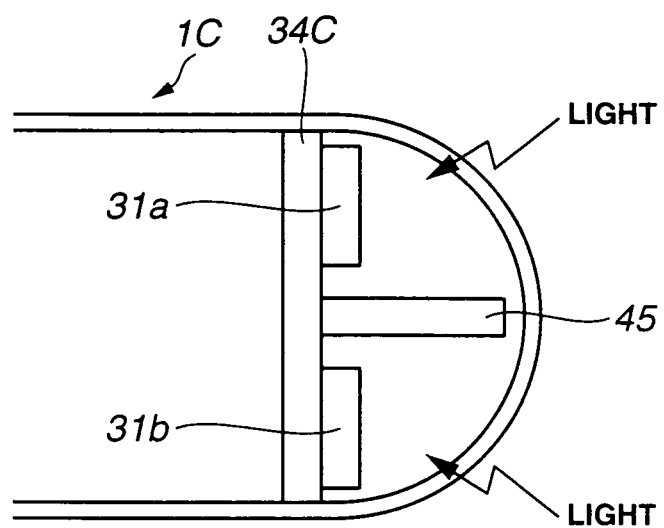
FIG. 6 is a schematic diagram showing a main portion of a capsule medical apparatus according to a third embodiment of the present invention.

FIG. 6 shows a main portion of a capsule medical apparatus 1C according to the third embodiment. According to the third embodiment, a switch circuit 34C for supplying and stopping the power comprises two optical sensors 31a and 31b. A shielding member 45 for shielding the light is arranged between the two optical sensors so as to prevent the incident state of light for setting one optical sensor to the on-state or off-state on the other optical sensor.

According to the third embodiment, the same advantages according to the first embodiment are obtained. Further, the same type of sensors are used, thereby reducing costs. Furthermore, in the case of ON-operation and OFF-operation, light-emitting means of one type of light controls the ON-operation and the OFF-operation, thereby improving the convenience.

Figure 7:
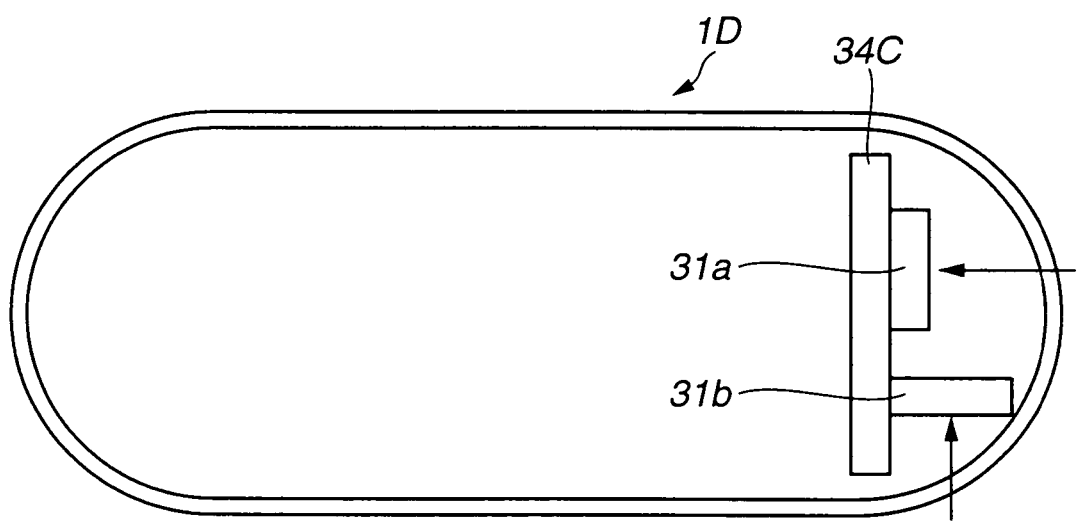
FIG. 7 is a diagram showing the schematic structure of a capsule medical apparatus according to a first modification of the third embodiment.

FIG. 7 shows a first modification of third embodiment shown in FIG. 6.

A capsule medical apparatus 1D according to the first modification of third embodiment has the optical sensors 31a and 31b shown in FIG. 6 which have different detecting directions of light.

For example, the one optical sensor 31a is arranged to detect the incident light from the longitudinal direction of the capsule medical apparatus 1D. The other optical sensor 31b is arranged to detect the incident light from the perpendicular direction of the longitudinal direction of the capsule medical apparatus 1D. Thus, the erroneous operation is prevented.

Figure 8:
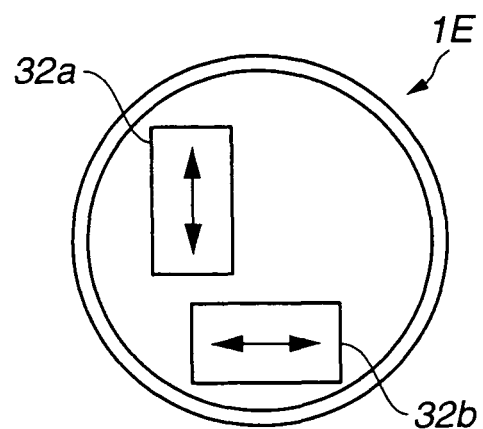
FIG. 8 is a diagram schematically showing the arrangement of sensors according to a second modification of the third embodiment.

Although the two optical sensors 31a and 31b are used as shown in FIGS. 6 and 7, magnetic sensors may be used. Referring to FIG. 8, a capsule medical apparatus 1E according to a second modification of third embodiment uses magnetic sensors 32a and 32b. The arrangement directions of the magnetic sensors 32a and 32b may be set to detect the mutually-perpendicular magnetic fields as shown in FIG. 8.

Figure 9:
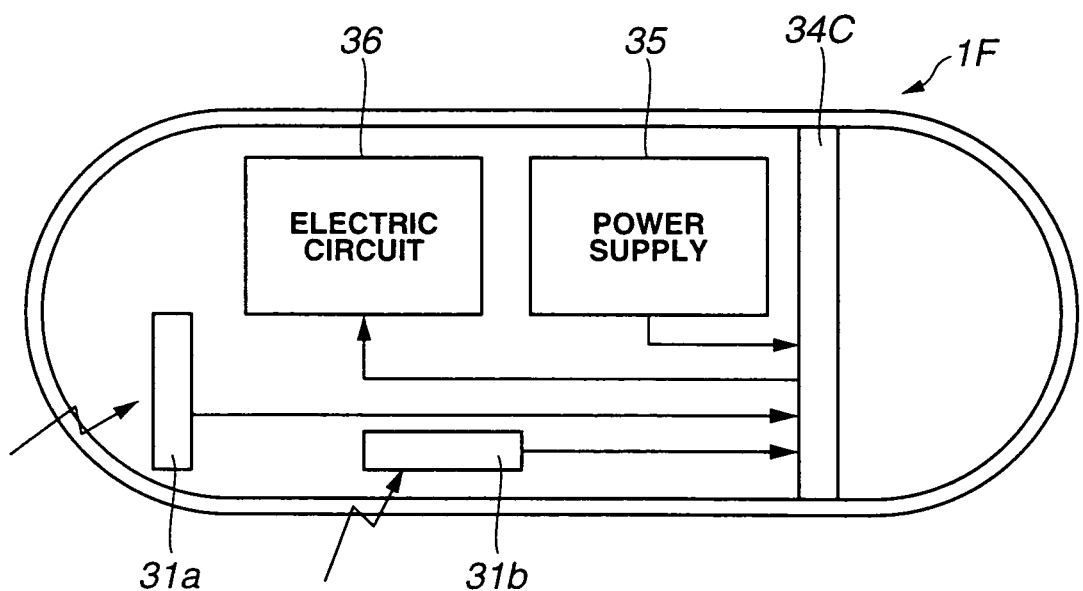
FIG. 9 is a diagram schematically showing the arrangement of sensors according to a third modification of the third embodiment.
Figure 10:
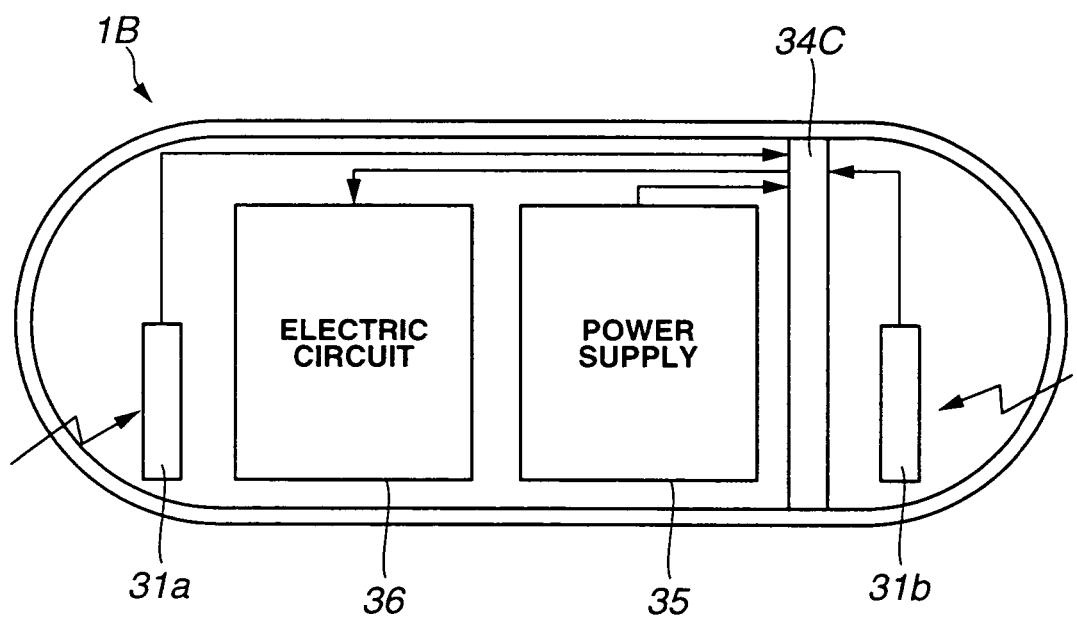
FIG. 10 is a diagram schematically showing the arrangement of sensors according to a fourth modification of the third embodiment.

FIGS. 9 and 10 show capsule medical apparatuses 1F and 1G according to third and fourth modifications of third embodiment.

Referring to FIGS. 9 and 10, the two optical sensors 31a and 31b are arranged at different positions.

For example, referring to FIG. 9, according to the third modification of third embodiment, the one optical sensor 31a is arranged at one end side of the main body, and the other optical sensor 31b is arranged near the side surface. Referring to FIG. 10, according to the fourth modification of third embodiment, the one optical sensor 31a is arranged to one end side of the main body, and the other optical sensor 31b is arranged to another end side.

The operations and advantages according to the third and fourth modifications are similar to those according to the third embodiment or the first modification of third embodiment shown in FIGS. 6 and 7.

According to the third and fourth modifications, as the one optical sensor (e.g., 31a), a CMOS sensor for image pickup operation may be used commonly to an optical sensor for on-operation. Or, a pixel portion, which is not used for image pickup operation in an image pickup device, such as a CMOS sensor, that is, is not necessary for image pickup operation, may be used as an optical sensor for on-operation. Thus, the number of sensors is reduced, and the costs and size are reduced.

(Fourth Embodiment)

Figure 11:
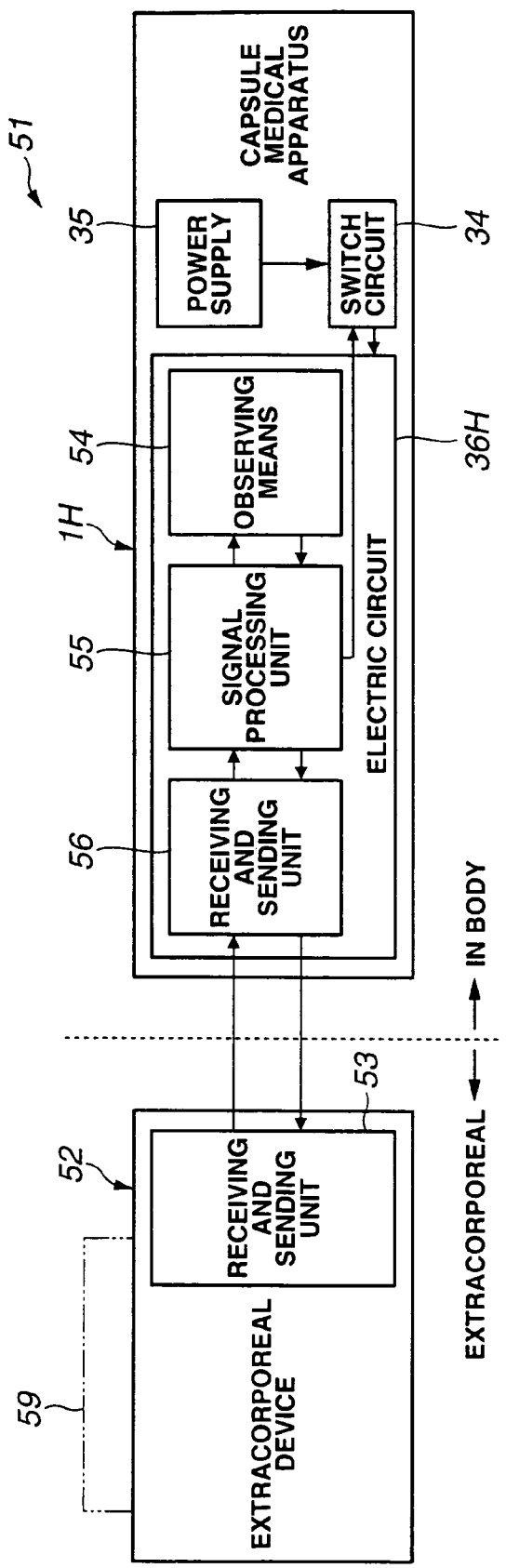
FIG. 11 is a diagram showing the entire structure of a capsule medical system having a capsule medical apparatus according to a fourth embodiment of the present invention.

Next, a description is given of the fourth embodiment with reference to FIG. 11. FIG. 11 shows a capsule medical system 51 having a capsule medical apparatus 1H according to the fourth embodiment of the present invention.

The system 51 comprises a main portion comprising the capsule medical apparatus 1H that is inserted in the body of a patient according to the fourth embodiment and an extracorporeal device 52 for wireless communication in the direction interactive to the capsule medical apparatus 1H.

The extracorporeal device 52 comprises a receiving and sending unit 53 that receives and sends a signal by wireless manner from/to the capsule medical apparatus 1H. Further, the capsule medical apparatus 1H comprises: observing means 54 for observation by an image pickup device; a signal processing unit 55 that performs signal processing of the observing means 54; and a receiving and sending unit 56 that sends the signal subjected to the signal processing by the signal processing unit 55 or receives the signal from the receiving and sending unit 53.

The capsule medical apparatus 1H comprises the switch circuit 34, the power supply 35, and an electric circuit 36H. The switch circuit 34 comprises the two sensors 31 and 32, like the switch circuit 34 in FIG. 3. Hereinbelow, a description is given of the magnetic sensor 31 for on-operation and the optical sensor 32 for off-operation.

One magnetic field is inputted to one magnetic sensor (magnetic sensor for ON-operation) 31, thereby setting the electric circuit 36H from the OFF-state to the ON-state via the switch circuit 34. The other optical sensor (optical sensor for OFF-operation) 32 is irradiated with light, thereby setting the electric circuit 36H from the ON-state to the OFF-state via the switch circuit 34.

According to the fourth embodiment, an instructing signal for OFF-operation is sent to the capsule medical apparatus 1H via the receiving and sending unit 53 from the external extracorporeal device 52. Thus, the signal processing unit 55 forming the electric circuit 36H enables an LED (not shown) to emit light. The light is incident on the optical sensor 31b for OFF-operation, thereby setting the switch circuit 34 from the ON-operation to the OFF-operation.

After swallowing the capsule medical apparatus 1H, the power is turned on by the irradiation with the external atmospheric physical quantity, or the power is turned off by the operation from the extracorporeal device 52. The power is turned off if unnecessary and is turned on if necessary while checking information transmitted from the capsule medical apparatus 1H, thereby saving the power consumption.

According to the fourth embodiment, in addition to the operations and advantages according to the first embodiment, the instructing signal is externally sent by wireless manner, thereby setting the capsule medical apparatus 1H to the OFF-operation and improving the convenience.

Referring to FIG. 11, the capsule medical apparatus may have generating means 59, as shown by a broken line. The generating means 59 generates a magnetic field or light for affecting the magnetic sensors for ON-operation and OFF-operation of the switch circuit 34. Specifically, the generating means 59 is a switch (using the power of the extracorporeal device 52) for ON/OFF operation of light emission of an electromagnet such as a coil and/or LED.

Although the two sensors are arranged in the above description, a capsule medical apparatus may have a sensor that sets the ON-operation and the OFF-operation by the input of the atmospheric physical quantity to one sensor.

For example, in the capsule medical apparatus 1B according to the second embodiment, the power of the capsule medical apparatus 1B after being swallowed may be turned on/off by extracorporeally applying the magnetic field.

In a system having the extracorporeal device 52 in this case, an instruction for externally turning-off the power by wireless manner is not necessary. Thus, the receiving and sending unit 53 in the extracorporeal device 52 may be used as a receiving unit, and the receiving and sending unit 56 in the capsule medical apparatus 1B may be used as a sending unit, resulting in a simple structure.

(Fifth Embodiment)

Figure 12A:
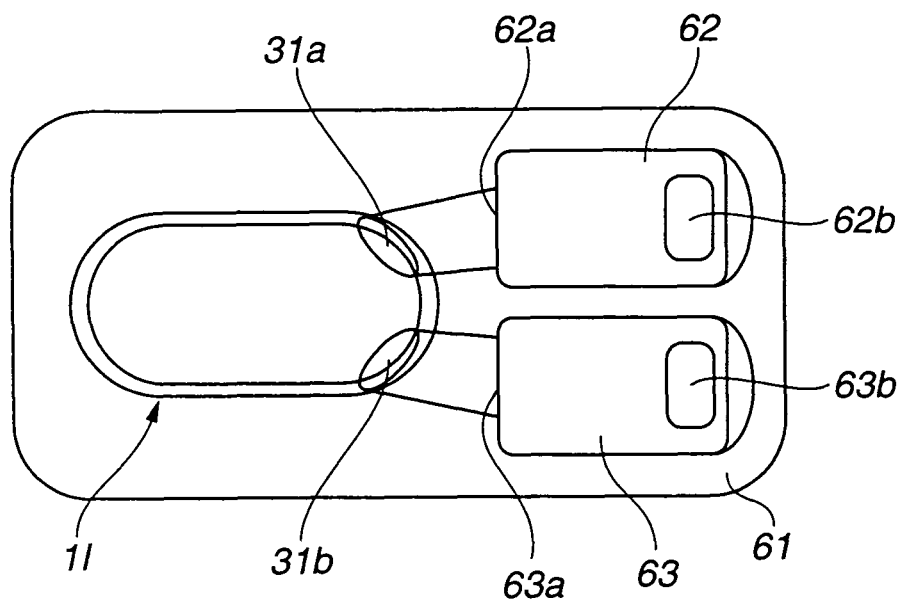
FIG. 12A is a plan view schematically showing a capsule medical apparatus according to a fifth embodiment of the present invention.
Figure 12B:
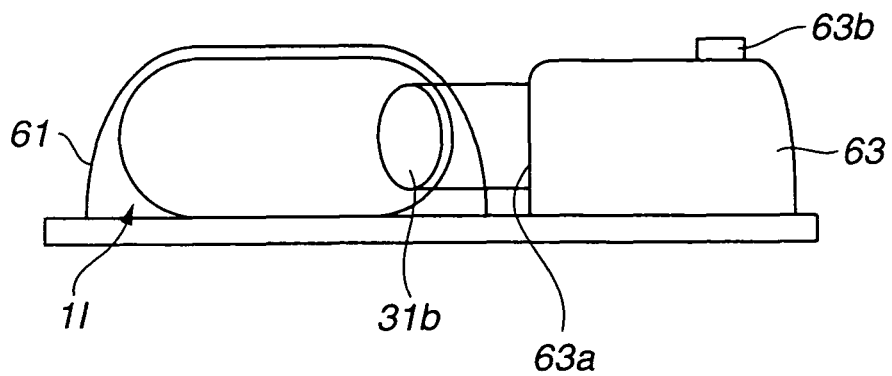
FIG. 12B is a side view schematically showing a capsule medical apparatus according to a fifth embodiment of the present invention.

Next, a description is given of the fifth embodiment with reference to FIG. 12. FIGS. 12A and 12B show a capsule medical apparatus 1I according to the fifth embodiment of the present invention. FIG. 12A shows a plan view, and FIG. 12B shows a side view.

The capsule medical apparatus 1I is covered and packed with a package 61 sterilized before use. The capsule medical apparatus 1I includes the optical sensor 31a for ON-operation and the optical sensor 31b for OFF-operation. In the packed state, the capsule medical apparatus 1I comprises a light generating unit 62 for ON-operation and a light generating unit 63 for OFF-operation having LEDs 62a and 63a for generating the light for ON-operation and the light for OFF-operation, facing transmitting windows of the optical sensor for ON-operation and the optical sensor for OFF-operation.

On the top of the light generating unit 62 for ON-operation and the light generating unit 63 for OFF-operation, switches 62b and 63b for operation are arranged. The switch 62b for operation is pressed and, thus, the power is supplied to the LED 62a from the included power supply, so that the LED 62a emits light. The light is incident on the optical sensor for ON-operation, thereby turning-on the power of the capsule medical apparatus 1I.

The switch 63b for operation is pressed and, thus, the included power supply feeds the power to the LED 63a. The LED 63a emits the light. The light is incident on the optical sensor for OFF-operation, thereby turning-off the capsule medical apparatus 1I.

According to the fifth embodiment, advantageously, the operation of the capsule medical apparatus 1I in the sterilizing state is confirmed.

Figure 13:
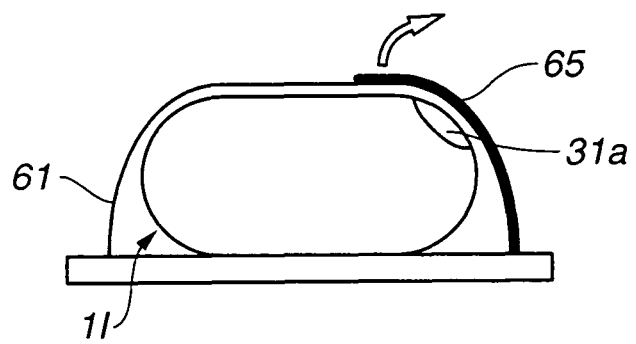
FIG. 13 is a diagram showing the schematic structure of a capsule medical apparatus according to a first modification of the fifth embodiment.

Referring to FIG. 13, according to a first modification of the fifth embodiment, a shielding member 65, such as a shielding tape, may adhere the transmitting window of the optical sensor 31a for ON-operation and the shielding member 65 may be detached, thereby turning on the capsule medical apparatus 1I by the detection of the optical sensor 31a for ON-operation with environmental light.

According to the first modification of the fifth embodiment, the light generating unit 62 for ON-operation is not necessary, thereby reducing the costs.

The package itself may contain a shielding member and may be detached, thereby turning on the capsule medical apparatus.

Figure 14:
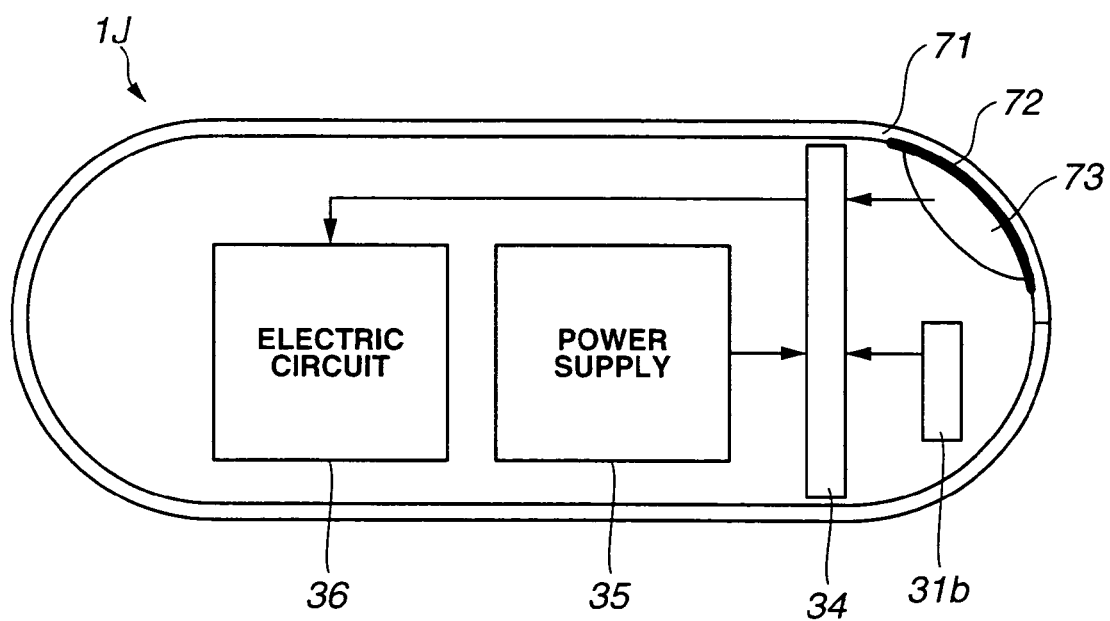
FIG. 14 is a diagram showing the schematic structure of a capsule medical apparatus according to a second modification of the fifth embodiment.

According to a second modification of the fifth embodiment, referring to FIG. 14, a capsule medical apparatus 1J comprises a temperature sensor 73 for ON-operation in a transparent exterior member 71. The temperature sensor 73 for ON-operation is set to have a predetermined temperature by dipping in the hot water of 50°, thereby switching-on a switch of the switch circuit 34.

According to the second modification, a coating material that changes in color at a temperature is coated by adhering a temperature color-changing sheet 72 that changes in color at the predetermined temperature to the inside of the transparent exterior member 71, such as the outside of the temperature sensor 73. It is easily determined, based on the color change of the temperature color-changing sheet 72, whether or not the capsule medical apparatus 1J has been used for medical action.

Figure 15:
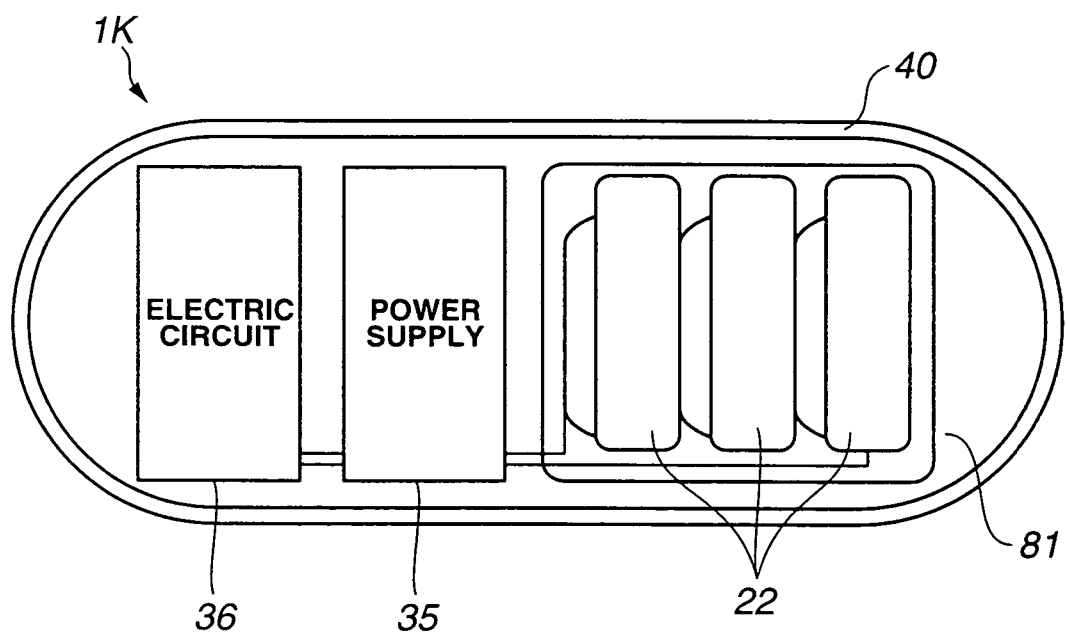
FIG. 15 is a diagram showing the schematic structure of a capsule medical apparatus according to a third modification of the fifth embodiment.

In a capsule medical apparatus 1K according to a third modification of the fifth embodiment shown in FIG. 15, the included batteries 22 may watertightly be covered with coating or a container 81. Further, the batteries 22 and a power line (not shown) connected thereto may watertightly be covered with a coating or a container. Then, when the exterior member 40 is temporarily broken and the watertight state is not held, it is possible to prevent the body fluid from coming in immediate contact with an electronic part such as the batteries 22.

Another embodiment structured by partly combining the above-mentioned embodiments belongs to the present invention.

In addition to the embodiments, a sound-wave detecting sensor, such as a microphone for detecting the sound waves (including ultrasonic sound waves) may be used, or a sensor for detecting the electromagnetic waves may be used.

That is, it is possible to widely use a sensor for detecting the change in atmospheric physical quantity, such as the magnetic force, light, sound waves, temperature, and electromagnetic waves.

According to the embodiments and modifications, the atmospheric physical quantity generated outside of the capsule exterior member includes the magnetic force, light, sound waves, temperature, and electromagnetic waves. However, the present invention is not limited to this, and another atmospheric physical quantity on the capsule medical apparatus may include the atmospheric physical quantity of a predetermined component of a material that externally exists.

In the medical action, to which the capsule medical apparatus according to the present invention is applied, the capsule shape of the capsule medical apparatus is preferably suitable to the inspection, treatment, and various curing in view of the inspection, treatment, and various curing in the body of the examinee.

Any embodiment structured by partly combining the above-mentioned embodiments belongs to the present invention.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A capsule medical apparatus comprising:
a capsule exterior member;
an electric circuit arranged in the exterior member;

a battery arranged in the exterior member; and a switch circuit for controlling to switch a state of energy supply from the battery to the electric circuit to one of an ON-state and OFF-state;

wherein the switch circuit includes:

a first physical quantity detecting unit which can detect a temporary change of a first physical quantity outside the exterior member and which, upon detecting the temporary change of the first physical quantity, starts the energy supply from the battery;

a second physical quantity change detecting unit which can detect a temporary change of a second physical quantity outside the exterior member and which, upon detecting the temporary change of the second physical quantity, stops the energy supply from the battery; and a power supply state holding unit which holds the state of energy supply from the battery to the electric circuit to the OFF-state until the first physical quantity change detecting unit detects the temporary change of the first physical quantity, and holds the state of energy supply from the battery to the electric circuit to the ON-state until the second physical quantity change detecting unit detects the temporary change of the second physical quantity; and wherein the first physical quantity and the second physical quantity are physical quantities of different types from each other.

2. A capsule medical apparatus according to claim 1, wherein the capsule exterior member has a shape suitable for the medical action.

3. A capsule medical apparatus according to claim 2, wherein the medical action is at least one of the inspection, treatment, and curing in the body of an examinee.

4. A capsule medical apparatus according to claim 1, wherein the change of the atmospheric physical quantity generated outside the exterior member, which is detected by the first and second physical quantity change detecting units, is at least one of the change of the magnetic field, light, sound waves, temperature, and electromagnetic waves.

5. A capsule medical apparatus according to claim 1, wherein the first and second physical quantity change detecting units comprise a plurality of sensor units that independently detect the change of the atmospheric physical quantities of different types from each other outside the exterior member.

6. A capsule medical apparatus according to claim 5, wherein the plurality of sensor units are two sensor units corresponding to the first physical quantity detecting unit and the second physical quantity detecting unit of the switch circuit.

7. A capsule medical apparatus according to claim 1, wherein the switch circuit can alternate the ON-state and the OFF-state based on the temporary change of the atmospheric physical quantity.

8. A capsule medical apparatus according to claim 7, wherein the change of the atmospheric physical quantity generated outside the exterior member, which is detected by the first and second physical quantity change detecting units, is at least one of a magnetic field, light, sound waves, temperature, and electromagnetic waves.

9. A capsule medical apparatus according to claim 7, wherein the switch circuit comprises a pulse dividing circuit which can alternate the ON-state and the OFF-state based on the temporary change of the atmospheric physical quantity.

* * * * *